(12) United States Patent
Lee

(10) Patent No.: US 8,849,414 B2
(45) Date of Patent: Sep. 30, 2014

(54) SYSTEMS AND METHODS FOR MAKING AND USING BENDABLE PADDLES WITH IMPLANTABLE ELECTRICAL STIMULATION SYSTEMS

(75) Inventor: Dongchul Lee, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 260 days.

(21) Appl. No.: 12/985,896

(22) Filed: Jan. 6, 2011

(65) Prior Publication Data

US 2011/0172751 A1 Jul. 14, 2011

Related U.S. Application Data

(60) Provisional application No. 61/294,983, filed on Jan. 14, 2010.

(51) Int. Cl.
*A61N 1/05* (2006.01)
(52) U.S. Cl.
CPC ..................................... *A61N 1/0553* (2013.01)
USPC .............................. 607/115; 607/45; 607/116
(58) Field of Classification Search
USPC .............................. 607/45, 46, 115, 116, 117
See application file for complete search history.

(56) References Cited

U.S. PATENT DOCUMENTS

| | | | |
|---|---|---|---|
| 6,181,969 B1 | 1/2001 | Gord | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 7,177,702 B2 * | 2/2007 | Wallace et al. | 607/117 |
| 7,244,150 B1 | 7/2007 | Brase et al. | |
| 7,437,193 B2 | 10/2008 | Parramon et al. | |
| 2007/0150036 A1 | 6/2007 | Anderson | |
| 2008/0071320 A1 | 3/2008 | Brase | |

* cited by examiner

*Primary Examiner* — Joseph Dietrich
(74) *Attorney, Agent, or Firm* — Lowe Graham Jones PLLC; Patrick R. Turner

(57) ABSTRACT

An implantable paddle lead includes a paddle body coupled to a distal end of an elongated lead body. A plurality of contacts are disposed on a front surface of the paddle body. At least one manually bendable shape-retaining member is interconnected with the paddle body. The at least one shape-retaining member is formed from a deformable material that is stiff enough to maintain a given shape for at least one day. The at least one bendable shape-retaining member is interconnected with the paddle body such that bending the at least one shape-retaining member causes a corresponding bend of at least a portion of the paddle body in proximity to the at least one shape-retaining member.

19 Claims, 11 Drawing Sheets

SYSTEMS AND METHODS FOR MAKING AND USING BENDABLE PADDLES WITH IMPLANTABLE ELECTRICAL STIMULATION SYSTEMS

CROSS-REFERENCE TO RELATED APPLICATIONS

This application claims the benefit under 35 U.S.C. §119 (e) of U.S. Provisional Patent Application Ser. No. 61/294,983 filed on Jan. 14, 2010, which is incorporated herein by reference.

FIELD

The present invention is directed to the area of implantable electrical stimulation systems and methods of making and using the systems. The present invention is also directed to implantable electrical stimulation leads having bendable paddles, as well as methods of making and using the paddles and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, an implantable paddle lead includes an elongated lead body with a proximal end and a distal end. A plurality of terminals are disposed at the proximal end of the lead body. A paddle body is coupled to the distal end of the lead body. The paddle body has a length, a width, and front surface. A plurality of contacts are disposed on the front surface of the paddle body. At least one manually bendable shape-retaining member is interconnected with the paddle body. The at least one shape-retaining member is formed from a deformable material that is stiff enough to maintain a given shape for at least one day. The at least one bendable shape-retaining member is interconnected with the paddle body such that bending the at least one shape-retaining member causes a corresponding bend of at least a portion of the paddle body in proximity to the at least one shape-retaining member. The implantable paddle lead also includes a plurality of conductors, each conductor electrically coupling at least one of the contacts to at least one of the terminals.

In another embodiment, a method for implanting a paddle lead into a patient includes providing a paddle lead, the paddle lead including: an elongated lead body with a proximal end and, a distal end, a plurality of terminals disposed on the proximal end of the lead body; and a substantially-planar paddle body coupled to the distal end of the lead body. The paddle body has a length, a width, and front surface. A plurality of contacts are disposed on the front surface of the paddle body. At least one bendable shape-retaining member is interconnected with the paddle body. The at least one shape-retaining member is formed from a deformable material that is stiff enough to maintain a given shape for an implantable lifetime of the paddle lead. The paddle lead also includes a plurality of conductors, each conductor electrically coupling at least one of the contacts to at least one of the terminals. The at least one shape-retaining member is bent to conform to at least a portion of an anatomical structure within the patient. Bending the at least one shape-retaining member causes a corresponding bend of at least a portion of the substantially-planar paddle body in proximity to the at least one shape-retaining member. The paddle lead is inserted into the patient such that at least a portion of the paddle body abuts the anatomical structure.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads having paddles, as well as methods of making and using the paddles and electrical stimulation systems.

Suitable implantable electrical stimulation systems include, but are not limited to, a paddle lead ("lead") with one or more electrodes disposed on a distal end of the lead and one or more terminals disposed on one or more proximal ends of the lead. Examples of electrical stimulation systems with paddle leads are found in, for example, U.S. Pat. Nos. 6,181,969; 6,516,227; 6,609,029; and 6,609,032; and U.S. Patent Applications Publication Nos. 2007/0150036; 2007/0161294; and 2008/0071320, all of which are incorporated by reference.

Figure 1:
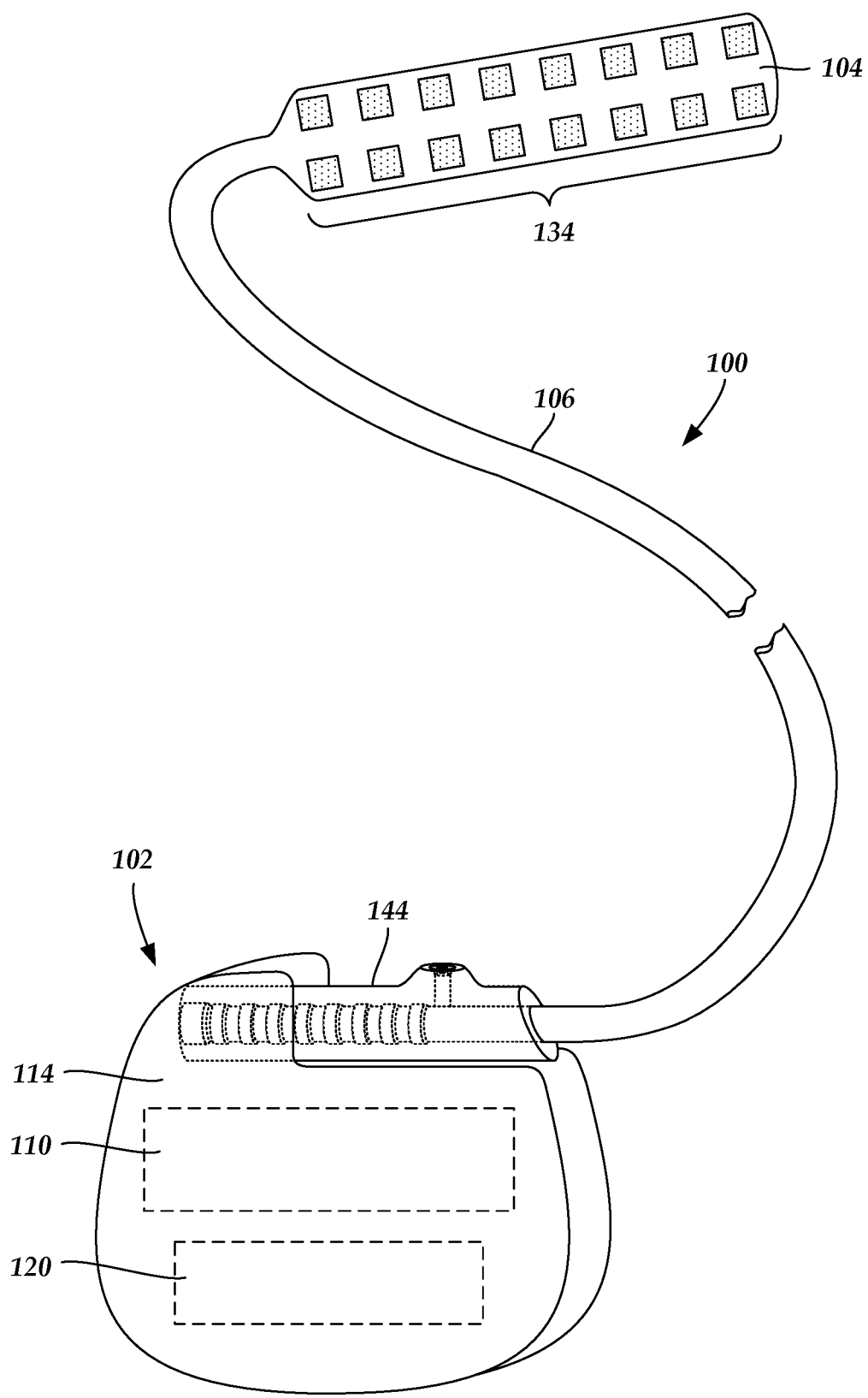
FIG. 1 is a schematic view of one embodiment of an electrical stimulation system that includes an array of electrodes disposed on a paddle body, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIGS. 2 and 3A, see also 322 and 350 of FIG. 3B) into which the proximal end of the one or more lead bodies 106 can be plugged to make an electrical connection via conductive contacts on the control module 102 and terminals (e.g., 310 in FIG. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, one or more lead extensions 312 (see FIG. 3B) can be disposed between the one or more lead bodies 106 and the control module 102 to extend the distance between the one or more lead bodies 106 and the control module 102 of the embodiments shown in FIG. 1.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, polyetheretherketone ("PEEK"), epoxy, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 210 in FIG. 2A and 236 of FIG. 2B) are typically disposed at the proximal end of the one or more lead bodies 106 for connection to corresponding conductive contacts (e.g., 214 in FIG. 2A and 240 of FIG. 2B) in connectors (e.g., 144 in FIGS. 1-2A and 222 and 250 of FIG. 2B) disposed on, for example, the control module 102 (or to other devices, such as conductive contacts on a lead extension, an operating room cable, or an adaptor). Conductive wires ("conductors") (not shown) extend from the terminals (e.g., 210 in FIG. 2A and 236 of FIG. 2B) to the electrodes 134.

Figure 2A:
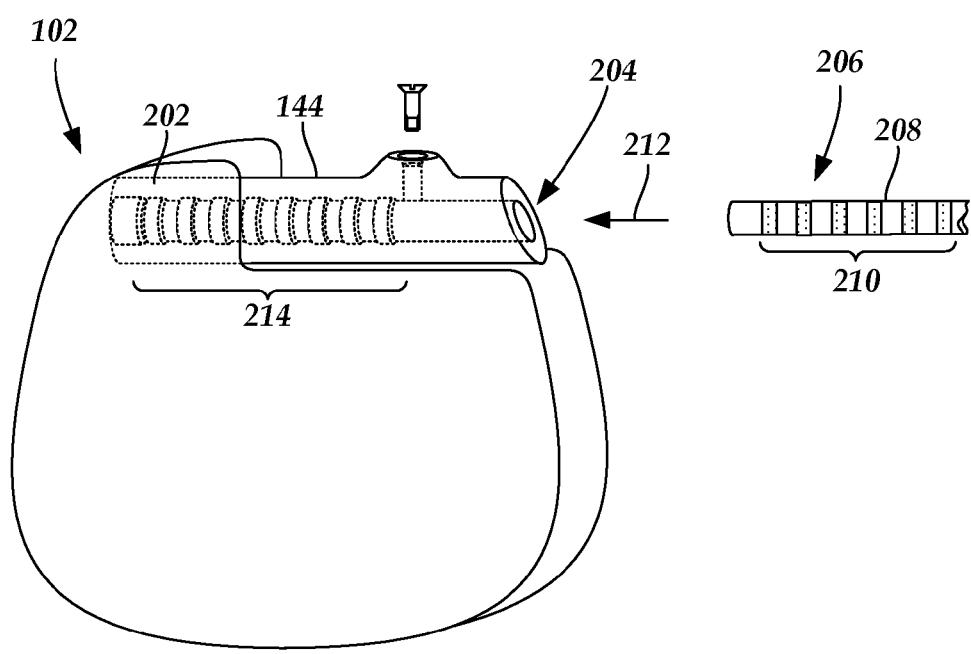
FIG. 2A is a schematic view of one embodiment of a proximal portion of a lead and a control module of an electrical stimulation system, according to the invention.
Figure 2B:
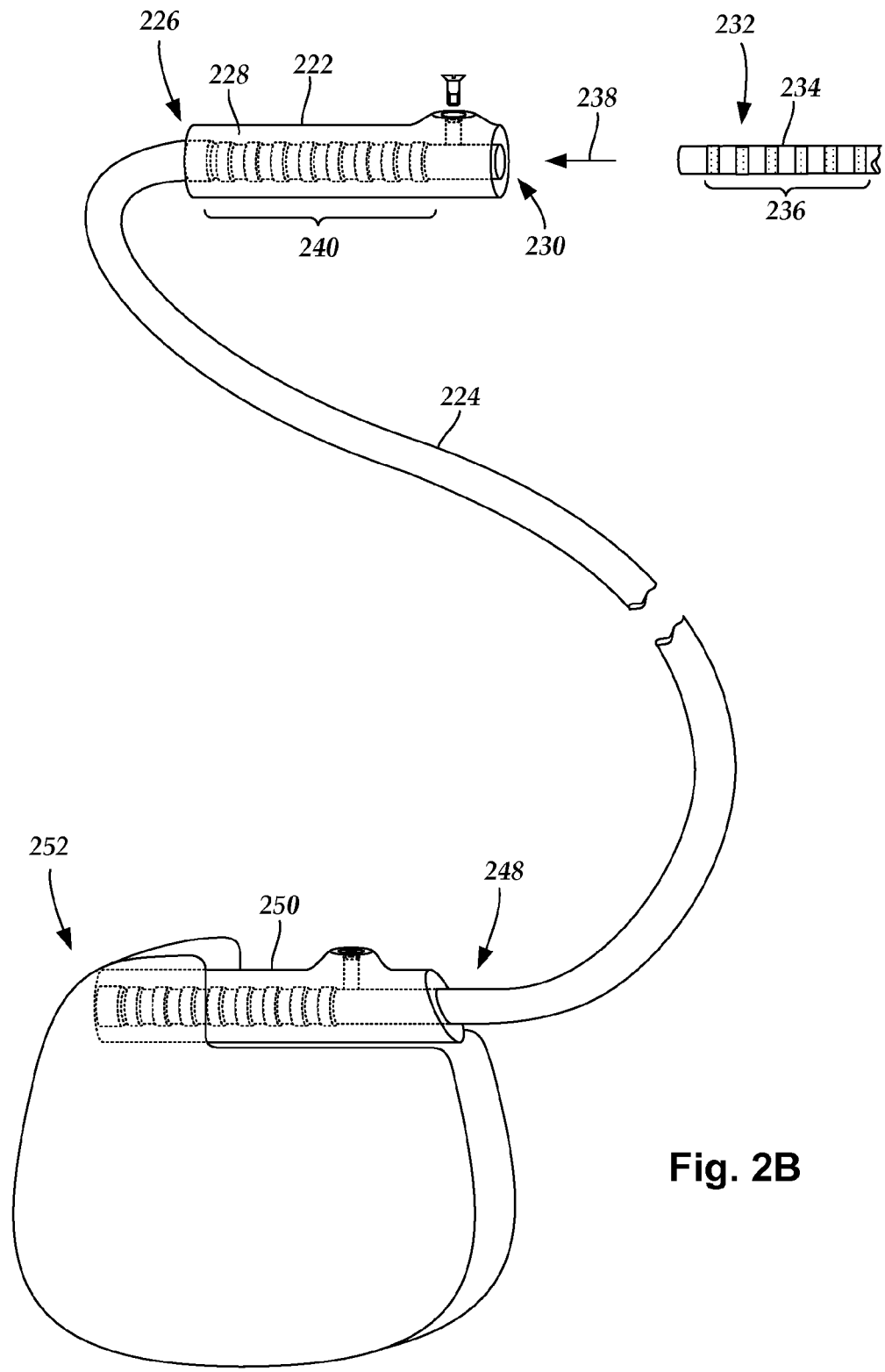
FIG. 2B is a schematic view of one embodiment of a proximal portion of a lead and a lead extension of an electrical stimulation system, according to the invention.

Typically, one or more electrodes 134 are electrically coupled to a terminal (e.g., 210 in FIG. 2A and 236 of FIG. 2B). In some embodiments, each terminal (e.g., 210 in FIG. 23A and 236 of FIG. 2B) is only connected to one electrode 134. The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

In at least some embodiments, leads are coupled to connectors disposed on control modules. In FIG. 2A, a lead 208 is shown configured and arranged for insertion to the control module 102. The connector 144 includes a connector housing 202. The connector housing 202 defines at least one port 204 into which a proximal end 206 of a lead 208 with terminals 210 can be inserted, as shown by directional arrow 212. The connector housing 202 also includes a plurality of conductive contacts 214 for each port 204. When the lead 208 is inserted into the port 204, the conductive contacts 214 can be aligned with the terminals 310 on the lead 208 to electrically couple the control module 102 to the electrodes (134 of FIG. 1) disposed at a distal end of the lead 208. Examples of connectors in control modules are found in, for example, U.S. patent application Ser. No. 11/532,844, which are incorporated by reference.

In FIG. 2B, a connector 222 is disposed on a lead extension 224. The connector 222 is shown disposed at a distal end 226 of the lead extension 224. The connector 222 includes a connector housing 228. The connector housing 228 defines at least one port 230 into which a proximal end 232 of a lead 234 with terminals 236 can be inserted, as shown by directional arrow 238. The connector housing 228 also includes a plurality of conductive contacts 240. When the lead 234 is inserted into the port 230, the conductive contacts 240 disposed in the connector housing 228 can be aligned with the terminals 236 on the lead 234 to electrically couple the lead extension 224 to the electrodes (134 of FIG. 1) disposed at a distal end (not shown) of the lead 234.

In at least some embodiments, the proximal end of a lead extension is similarly configured and arranged as a proximal end of a lead. The lead extension 224 may include a plurality of conductive wires (not shown) that electrically couple the conductive contacts 240 to a proximal end 248 of the lead extension 224 that is opposite to the distal end 226. In at least some embodiments, the conductive wires disposed in the lead extension 224 can be electrically coupled to a plurality of terminals (not shown) disposed on the proximal end 248 of the lead extension 224. In at least some embodiments, the proximal end 248 of the lead extension 224 is configured and arranged for insertion into a connector disposed in another lead extension. In other embodiments, the proximal end 248 of the lead extension 224 is configured and arranged for insertion into a connector disposed in a control module. As an example, in FIG. 2B the proximal end 248 of the lead extension 224 is inserted into a connector 250 disposed in a control module 252.

Paddle bodies are often implanted into a patient such that the paddle bodies abut one or more curved body structures which receive electrical stimulation. For example, when a paddle body is used for spinal cord stimulation, the paddle body may be inserted into the patient's epidural space at a desired level of the spinal cord such that the paddle body is in proximity to the dura mater, or dura, which surrounds the spinal cord.

At least some conventional paddle bodies are flat and formed from non-conductive materials that maintain a planar arrangement throughout the implanted lifetime of the paddle bodies. Unfortunately, disposing a flat paddle body into a curved space (e.g., an epidural space) may cause the paddle body to flatten at least a portion of the anatomical structure to conform to the flat shape of the paddle body, or to align electrodes disposed on the paddle body to the patient tissue to be stimulated. Moreover, disposing a flat paddle body against a curved structure (e.g., a dura) may create different propagation distances between different individual electrodes disposed on the planar paddle body and the stimulation target (e.g., a spinal cord) within the anatomical structure which the paddle body abuts. Creating different propagation distances between different individual electrodes disposed on a paddle body may reduce the efficacy of electrical stimulation.

A bendable paddle body ("paddle body") includes one or more deformable shape-retaining members disposed along one or more portions of the paddle body, the shape-retaining members enabling the paddle body to maintain a desired shape. The shape-retaining members are interconnected to the paddle body such that the portion(s) of the paddle body in proximity to the shape-retaining member(s) form and maintain a shape that corresponds to the shape of the shape-retaining member(s). In at least some embodiments, the shape-retaining member(s) are disposed within the paddle body. In at least some embodiments, the shape-retaining member(s) are coupled externally to the paddle body. In at least some embodiments, at least a portion of the one or more shape-retaining members are disposed within the paddle body and at least a portion of the one or more shape-retaining members are disposed external to the paddle body.

The shape-retaining members are configured and arranged for being manually bent into a desired shape prior to implantation into a patient. In at least some embodiments, the shape-retaining members are provided in a flat configuration prior to implantation into a patient. In at least some embodiments, the shape-retaining members provided in a bent configuration prior to implantation into a patient.

In at least some embodiments, when the one or more shape-retaining members are manually bent into a given shape, the one or more shape-retaining members are configured and arranged to maintain the given shape throughout the operational lifetime of the paddle body. In at least some embodiments, when the one or more shape-retaining members are manually bent into a given shape, the one or more shape-retaining members are configured and arranged to maintain the given shape throughout the implantable lifetime of the paddle body within a patient. In at least some embodiments, when the one or more shape-retaining members are manually bent into a given shape, the one or more shape-retaining members are configured and arranged to maintain the given shape for at least one hour. In at least some embodiments, when the one or more shape-retaining members are manually bent into a given shape, the one or more shape-retaining members are configured and arranged to maintain the given shape for at least six hours. In at least some embodiments, when the one or more shape-retaining members are manually bent into a given shape, the one or more shape-retaining members are configured and arranged to maintain the given shape for at least twelve hours. In at least some embodiments, when the one or more shape-retaining members are manually bent into a given shape, the one or more shape-retaining members are configured and arranged to maintain the given shape for at least one day. In at least some embodiments, when the one or more shape-retaining members are manually bent into a given shape, the one or more shape-retaining members are configured and arranged to maintain the given shape for at least two days. In at least some embodiments, when the one or more shape-retaining members are manually bent into a given shape, the one or more shape-retaining members are configured and arranged to maintain the given shape for at least one week. In at least some embodiments, when the one or more shape-retaining members are manually bent into a given shape, the one or more shape-retaining members are configured and arranged to maintain the given shape for at least two weeks. In at least some embodiments, when the one or more shape-retaining members are manually bent into a given shape, the one or more shape-retaining members are configured and arranged to maintain the given shape for at least one month. In at least some embodiments, when the one or more shape-retaining members are manually bent into a given shape, the one or more shape-retaining members are configured and arranged to maintain the given shape for at least two months. In at least some embodiments, when the one or more shape-retaining members are manually bent into a given shape, the one or more shape-retaining members are configured and arranged to maintain the given shape for at least six months. In at least some embodiments, when the one or more shape-retaining members are manually bent into a given shape, the one or more shape-retaining members are configured and arranged to maintain the given shape for at least one year.

Figure 3A:
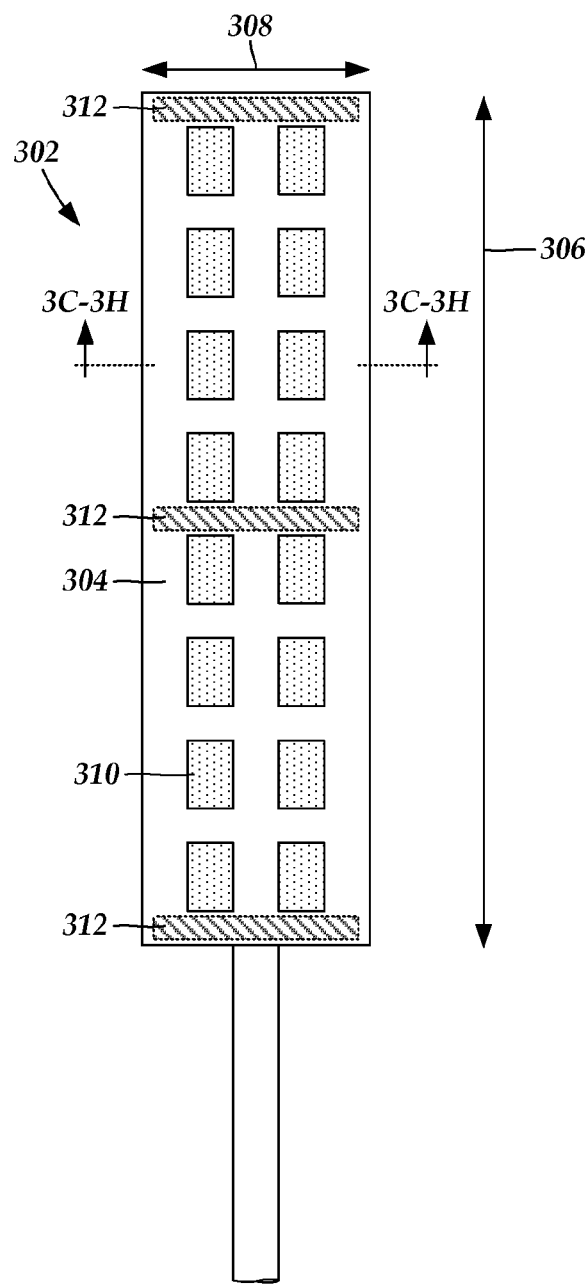
FIG. 3A is a schematic side view of one embodiment of a paddle body with shape-retaining members, according to the invention.

FIG. 3A is a schematic side view of one embodiment of a substantially-planar paddle body 302. The paddle body 302 includes a front face 304 and has a length (represented in FIG. 3A by two-headed arrow 306) and a width (represented in FIG. 3A by two-headed arrow 308). A plurality of electrodes, such as electrode 310, are disposed on the front face 304. One or more shape-retaining members 312 are disposed either within the paddle body 302, on an exterior surface of the paddle body 302, or both.

In at least some embodiments, the shape-retaining members 312 are formed from any material suitable for implantation that is pliable enough to be bent prior to implantation, yet stiff enough to maintain a given shape (e.g., one or more metals, alloys, composites, or the like or combinations thereof) under local conditions at an implantation location (e.g., body temperature, pressure, pH, exposure to internal or external forces, or the like).

In at least some embodiments, the shape-retaining members 312 become more flexible when heated. In at least some embodiments, the shape-retaining members 312 become more flexible when heated above room temperature. In at least some embodiments, the shape-retaining members 312 become more rigid when cooled. In at least some embodiments, the shape-retaining members 312 become more rigid when cooled below body temperature.

In at least some embodiments, once implanted, the shape-retaining members 312 maintain a given shape during normal activity. In at least some embodiments, once implanted, the shape-retaining members 312 are configured and arranged to flex during normal activity. In at least some embodiments, once implanted, the shape-retaining members 312 are flexible enough to bend during normal activity. In at least some embodiments, the shape-retaining members 312 (or portions of shape-retaining members 312) extending along the width of the paddle body 302 are more rigid than the shape-retaining members 312 (or portions of shape-retaining members 312) extending along the length of the paddle body 302.

In at least some embodiments, the shape-retaining members 312 are formed from material that is different from the material used to form the paddle body 302. In at least some embodiments, the shape-retaining members 312 are formed from material that is more stiff than the material used to form the paddle body 302. In at least some embodiments, the shape-retaining members 312 are formed from material that is at least 10% more stiff than the material used to form the paddle body 302. In at least some embodiments, the shape-retaining members 312 are formed from material that is at least 20% more stiff than the material used to form the paddle body 302. In at least some embodiments, the shape-retaining members 312 are formed from material that is at least 30% more stiff than the material used to form the paddle body 302. In at least some embodiments, the shape-retaining members 312 are formed from material that is at least 40% more stiff than the material used to form the paddle body 302. In at least some embodiments, the shape-retaining members 312 are formed from material that is at least 50% more stiff than the material used to form the paddle body 302. In at least some embodiments, the shape-retaining members 312 are formed from material that is at least 60% more stiff than the material used to form the paddle body 302. In at least some embodiments, the shape-retaining members 312 are formed from material that is at least 70% more stiff than the material used to form the paddle body 302. In at least some embodiments, the shape-retaining members 312 are formed from material that is at least 80% more stiff than the material used to form the paddle body 302. In at least some embodiments, the shape-retaining members 312 are formed from material that is at least 90% more stiff than the material used to form the paddle body 302. In at least some embodiments, the shape-retaining members 312 are formed from material that is at least twice as stiff than the material used to form the paddle body 302.

In at least some embodiments, the shape-retaining members 312 are formed from material such that, when the shape-retaining members 312 are bent, the shape-retaining members retain their bent shapes for at least 10% longer than the paddle body 302 would if the paddle body 302 was similarly bent. In at least some embodiments, the shape-retaining members 312 are formed from material such that, when the shape-retaining members 312 are bent, the shape-retaining members retain their bent shapes for at least 20% longer than the paddle body 302 would if the paddle body 302 was similarly bent. In at least some embodiments, the shape-retaining members 312 are formed from material such that, when the shape-retaining members 312 are bent, the shape-retaining members retain their bent shapes for at least 50% longer than the paddle body 302 would if the paddle body 302 was similarly bent. In at least some embodiments, the shape-retaining members 312 are formed from material such that, when the shape-retaining members 312 are bent, the shape-retaining members retain their bent shapes at least twice as long as the paddle body 302 would if the paddle body 302 was similarly bent. In at least some embodiments, the shape-retaining members 312 are formed from material such that, when the shape-retaining members 312 are bent, the shape-retaining members retain their bent shapes for at least five times as long as the paddle body 302 would if the paddle body 302 was similarly bent. In at least some embodiments, the shape-retaining members 312 are formed from material such that, when the shape-retaining members 312 are bent, the shape-retaining members retain their bent shapes for at least ten times as long as the paddle body 302 would if the paddle body 302 was similarly bent.

Figure 3B:
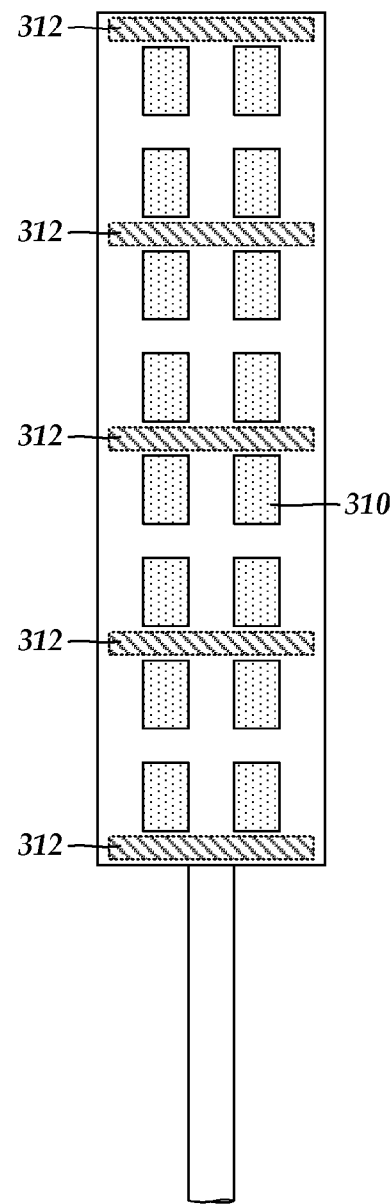
FIG. 3B is a schematic side view of another embodiment of a paddle body with shape-retaining members, according to the invention.

Any number of shape-retaining members 312 may be disposed in the paddle body 302 including, for example, one, two, three, four, five, six, seven, eight, nine, ten, eleven, twelve or more shape-retaining members 312. FIG. 3A shows three shape-retaining members disposed in the paddle body 302. FIG. 3B shows five shape-retaining members disposed in the paddle body. Additional figures show different numbers of shape-retaining members.

The shape-retaining members 312 may be formed in any desired shape. In at least some embodiments, the shape-retaining members 312 are formed as one or more material formed into one or more strips, rods, baton, slab, pin, stick, wand, shaft, spike, staff, stave, or the like. In at least some embodiments, the shape-retaining members are shown as one or more loops (or portions of loops) of material (see e.g., FIG. 5B).

Figure 3C:
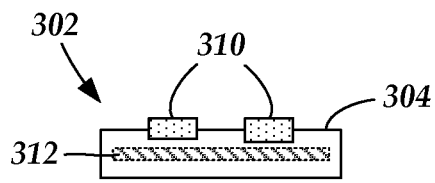
FIG. 3C is a schematic transverse cross-sectional view of one embodiment of the paddle body of FIG. 3A, according to the invention.

In at least some embodiments, the shape-retaining members 312 may be disposed in a flat configuration. FIG. 3C is a schematic transverse cross-sectional view of one embodiment of the paddle body 302 and one of the shape-retaining members 312 in a flat configuration. In at least some embodiments, one or more of the shape-retaining members 312 may be bent inwardly with respect to the front face 304 of the paddle body 302, the inward bend causing a corresponding inward bend of the paddle body 302 with respect to the front face 304. In at least some embodiments, one or more of the shape-retaining members 312 may be bent outwardly with respect to the front face 304, the outward bend causing a corresponding outward bend of the paddle body 302 with respect to the front face 304. In at least some embodiments, one or more of the shape-retaining members 312 may include a plurality of bends. In at least some embodiments, when one or more of the shape-retaining members 312 include a plurality of bends, at least one of the bends is an inward bend, with respect to the front face 304, and at least one of the bends is an outward bend, with respect to the front face 304.

In at least some embodiments, one or more of the shape-retaining members 312 may be manually bent by a health care professional during, or prior to, an implantation procedure. In at least some embodiments, one or more of the shape-retaining members 312 are bent with the aid of a tool or machine. In at least some embodiments, one or more of the shape-retaining members 312 are preformed into fixed shapes prior to being manually bent.

Figure 3F:
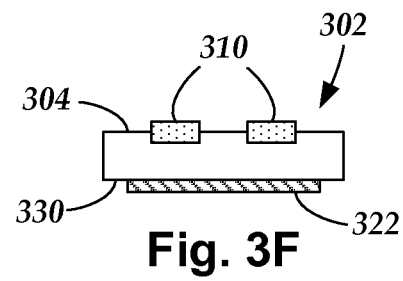
FIG. 3F is a schematic transverse cross-sectional view of another embodiment of the paddle body of FIG. 3A, according to the invention.
Figure 3D:
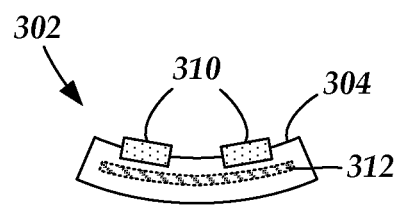
FIG. 3D is a schematic transverse cross-sectional view of one embodiment of the paddle body of FIG. 3C with an inwardly-bent shape-retaining member causing a corresponding bend in the paddle body, according to the invention.
Figure 3G:
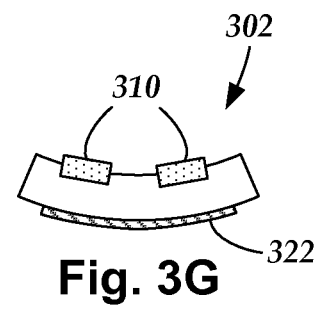
FIG. 3G is a schematic transverse cross-sectional view of one embodiment of the paddle body of FIG. 3F with an inwardly-bent shape-retaining member causing a corresponding bend in the paddle body, according to the invention.
Figure 3E:
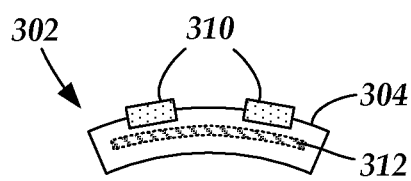
FIG. 3E is a schematic transverse cross-sectional view of one embodiment of the paddle body of FIG. 3C with an outwardly-bent shape-retaining member causing a corresponding bend in the paddle body, according to the invention.

FIG. 3D is a schematic transverse cross-sectional view of one embodiment of the paddle body 302 with inwardly-bent shape-retaining members 312, with respect to the front face 304 of the paddle body 302, causing corresponding bends in the paddle body 302. The inwardly-bent paddle body 302 causing the electrodes 310 to be directed inwardly. FIG. 3E is a schematic transverse cross-sectional view of one embodiment of the paddle body 302 with an outwardly-bent shape-retaining member 312, with respect to the front face 304, causing a corresponding bend in the paddle body 302. The outwardly-bent paddle body 302 causing the electrodes 310 to be directed outwardly.

In FIGS. 3C-3E, one of the shape-retaining members 312 is shown disposed completely within the paddle body 302. As discussed above, in at least some embodiments at least a portion of at least one of the shape-retaining members 312 can be disposed external to the paddle body 302. The shape-retaining members 312 may be coupled to any external surface(s) of the paddle body 302. In preferred embodiments, when the shape-retaining members 312 are disposed on one or more external surface of the paddle body 302, the one or more shape-retaining member do not contact the electrodes 310. In at least some embodiments, when the shape-retaining members 312 are disposed on one or more external surface of the paddle body 302, the one or more shape-retaining members do not obstruct propagation of electrical signals propagating from the electrodes 310.

FIG. 3F is a schematic transverse cross-sectional view of another embodiment of the paddle body 302 having external shape-retaining members 312. In FIG. 3F, the external shape-retaining members 322 are disposed on a rear face 330 of the paddle body 302 that is opposite to the front face 304. The external shape-retaining members 322 may be coupled to the paddle body 302 using any method of coupling suitable for implantation (e.g., one or more adhesives).

In at least some embodiments, the external shape-retaining members 322 may be bent inwardly with respect to the front face 304 of the paddle body 302. FIG. 3G is a schematic transverse cross-sectional view of another embodiment of the paddle body 302 with inwardly-bent external shape-retaining members 322, with respect to the front face 304 of the paddle body 302, causing corresponding bends in the paddle body 302. The inwardly-bent paddle body 302 causing the electrodes 310 to be directed inwardly.

Figure 3H:
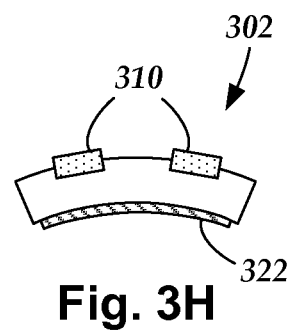
FIG. 3H is a schematic transverse cross-sectional view of another embodiment of the paddle body of FIG. 3F with an outwardly-bent shape-retaining member causing a corresponding bend in the paddle body, according to the invention.

In at least some embodiments, the external shape-retaining members 322 may be bent outwardly with respect to the front face 304 of the paddle body 302. FIG. 3H is a schematic transverse cross-sectional view of one embodiment of the paddle body 302 with outwardly-bent external shape-retaining members 322, with respect to the front face 304 of the paddle body 302, causing corresponding bends in the paddle body 302. The outwardly-bent paddle body 302 causing the electrodes 310 to be directed outwardly.

In FIGS. 3A-3H, each of the shape-retaining members are shown extending across the width 308 of the paddle body 302. In at least some embodiments, one or more of the shape-retaining members extend partially across the width 308 of the paddle body 302. In at least some embodiments, one or more of the shape-retaining members extend substantially across the width 308 of the paddle body 302. In at least some embodiments, one or more of the shape-retaining members extend substantially entirely across the width 308 of the paddle body 302. In at least some embodiments, one or more of the shape-retaining members extend across at least half of the width 308 of the paddle body 302. In at least some embodiments, one or more of the shape-retaining members extend across at least 60% of the width 308 of the paddle body 302. In at least some embodiments, one or more of the shape-retaining members extend across at least 75% of the width 308 of the paddle body 302. In at least some embodiments, one or more of the shape-retaining members extends across the entire width 308 of the paddle body 302.

Figure 4A:
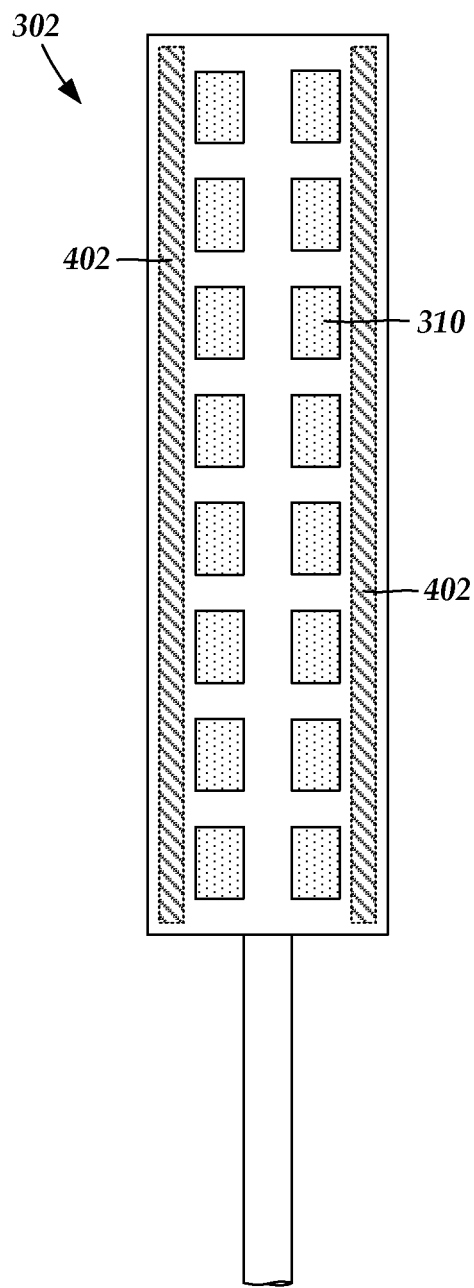
FIG. 4A is a schematic side view of yet another embodiment of a paddle body with shape-retaining members, according to the invention.

In at least some embodiments, one or more of the shape-retaining members may extend across at least a portion of the paddle body 302 in one or more other directions. FIG. 4A is a schematic side view of yet another embodiment of the paddle body 302 with shape-retaining members 402 disposed along the length 306 of the paddle body 302. In at least some embodiments, one or more of the shape-retaining members extend partially across the length 306 of the paddle body 302. In at least some embodiments, one or more of the shape-retaining members extend substantially across the length 306 of the paddle body 302. In at least some embodiments, one or more of the shape-retaining members extend substantially entirely across the length 306 of the paddle body 302. In at least some embodiments, one or more of the shape-retaining members extend across at least half of the length 306 of the paddle body 302. In at least some embodiments, one or more of the shape-retaining members extend across at least 60% of the length 306 of the paddle body 302. In at least some embodiments, one or more of the shape-retaining members extend across at least 75% of the length 306 of the paddle body 302. In at least some embodiments, one or more of the shape-retaining members extends across the entire length 306 of the paddle body 302.

Figure 4B:
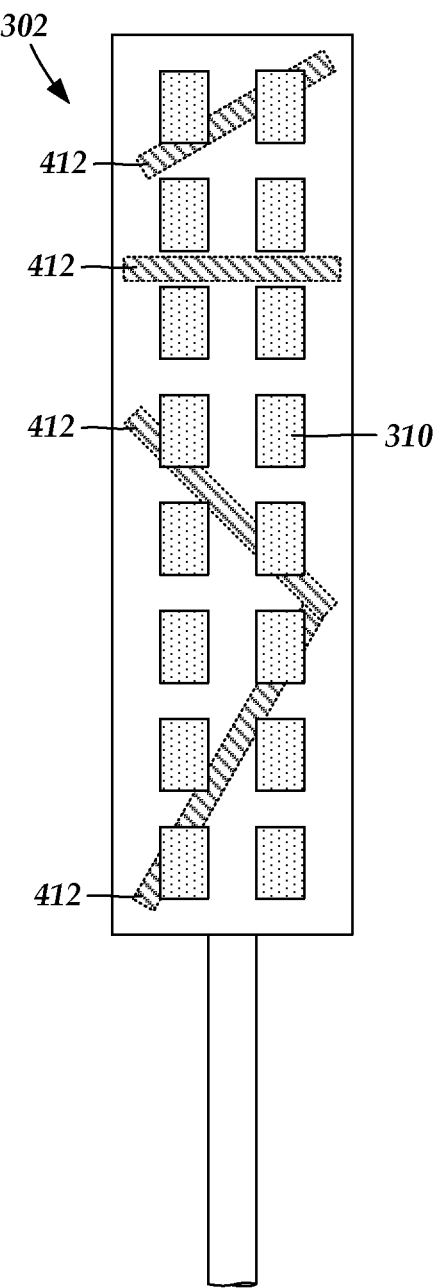
FIG. 4B is a schematic side view of another embodiment of a paddle body with shape-retaining members, according to the invention.

FIG. 4B is a schematic side view of another embodiment of the paddle body 302 with shape-retaining members 412 disposed along the paddle body 302 in a variety of different directions. In at least some embodiments, one or more of the shape-retaining members 412 may extend beneath one or more of the electrodes 310. In at least some embodiments, at least a portion of the one of the shape-retaining members 402 may overlap at least a portion of another of the shape-retaining members 402.

The electrodes 310 may be arranged on the front face 304 of the paddle body 302 in any suitable arrangement to provide therapeutic electrical stimulation. In at least some embodiments, the electrodes 310 are arranged into one or more rows. In at least some embodiments, the electrodes 310 are arranged into one or more columns. In FIGS. 3A-4B, the electrodes are shown in two columns.

Figures 5A, 5B:
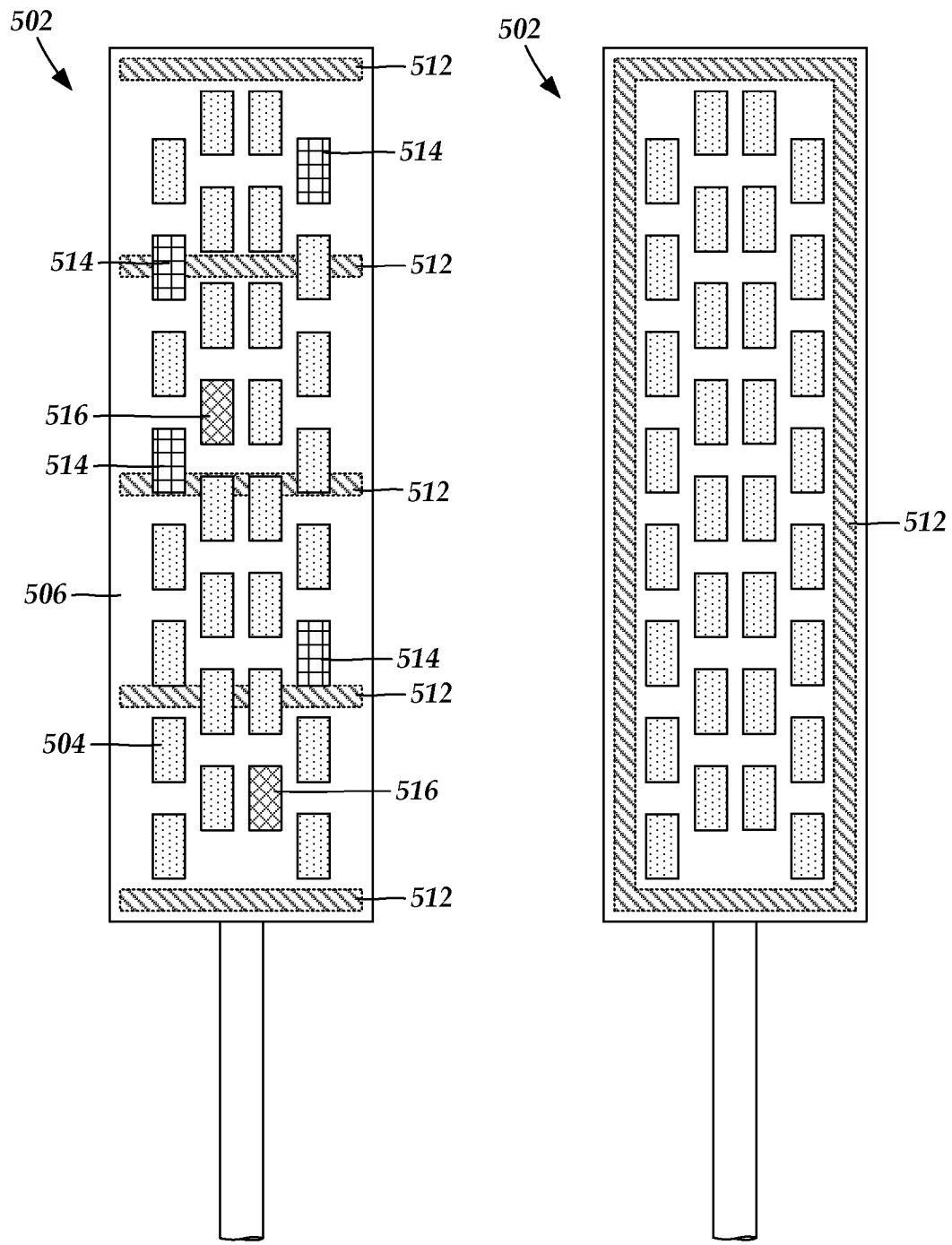
FIG. 5A is a schematic side view of yet another embodiment of a paddle body with shape-retaining members, according to the invention.
FIG. 5B is a schematic side view of another embodiment of a paddle body with a shape-retaining member, according to the invention.

FIG. 5A is a schematic side view of yet another embodiment of a paddle body 502 with electrodes, such as electrode 504, disposed on a front face 506 of the paddle body 502. The paddle body 502 also includes shape-retaining members 512 disposed in the paddle body 502. In FIG. 5A, the electrodes 504 are arranged into four columns.

In at least some embodiments, one or more of the electrodes 504 may be used for monopolar stimulation. In at least some embodiments, one or more of the electrodes 504 may be used for multipolar stimulation (e.g., tripolar, tetrapolar, or the like). In at least some embodiments, one or more of the electrodes 504 may operate as either an anode 514 or a cathode 516.

In at least some embodiments, the shape-retaining members may be formed as a loop of material. FIG. 5B is a schematic side view of another embodiment of the paddle body 502 with a shape-retaining member 512 formed as a continuous loop of material. In at least some embodiments, the loop of material extends around a portion of the paddle body 302. In at least some embodiments, the loop of material extends in proximity to one or more of the edges of the paddle body 502. In at least some embodiments, the loop of material extends in proximity to a perimeter of the paddle body 502. In at least some embodiments, one or more shape-retaining members 512 may form a plurality of loops of material along the paddle body 502. In other embodiments, one or more shape-retaining members 512 may be used to form one or more discontinuous loops along the paddle body 502. In at least some embodiments, the shape-retaining members may be C-shaped, U-shaped, horseshoe-shaped, or the like.

Figure 6A:
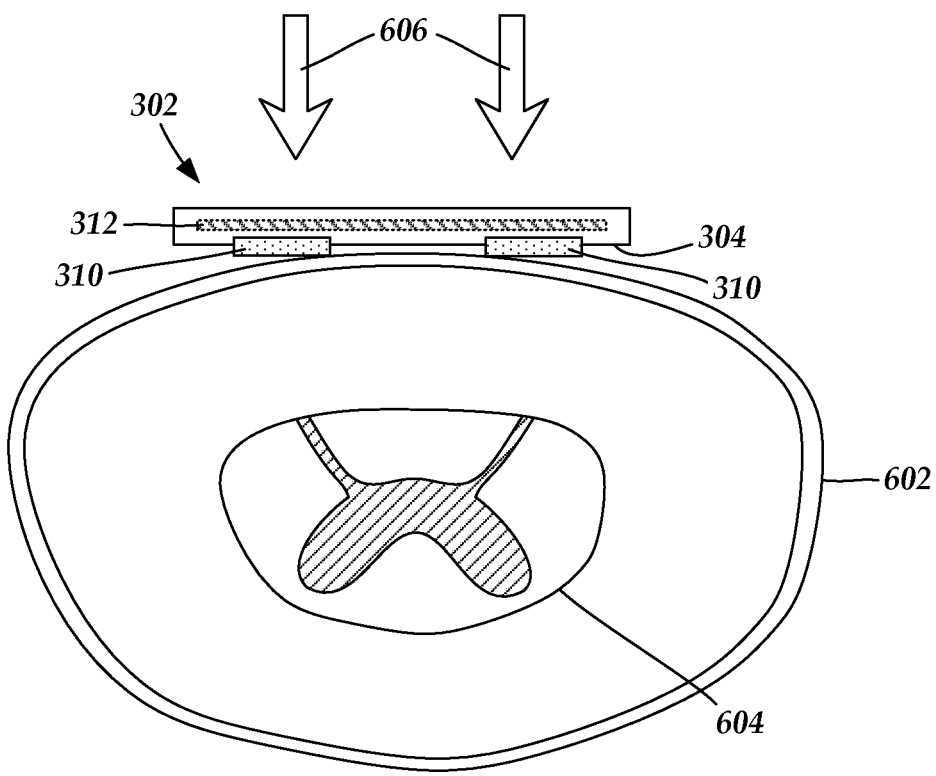
FIG. 6A is a schematic transverse cross-sectional view of the paddle body of FIG. 3A abutting a dura surrounding a spinal cord, the paddle body in a flat configuration, according to the invention.
Figure 6B:
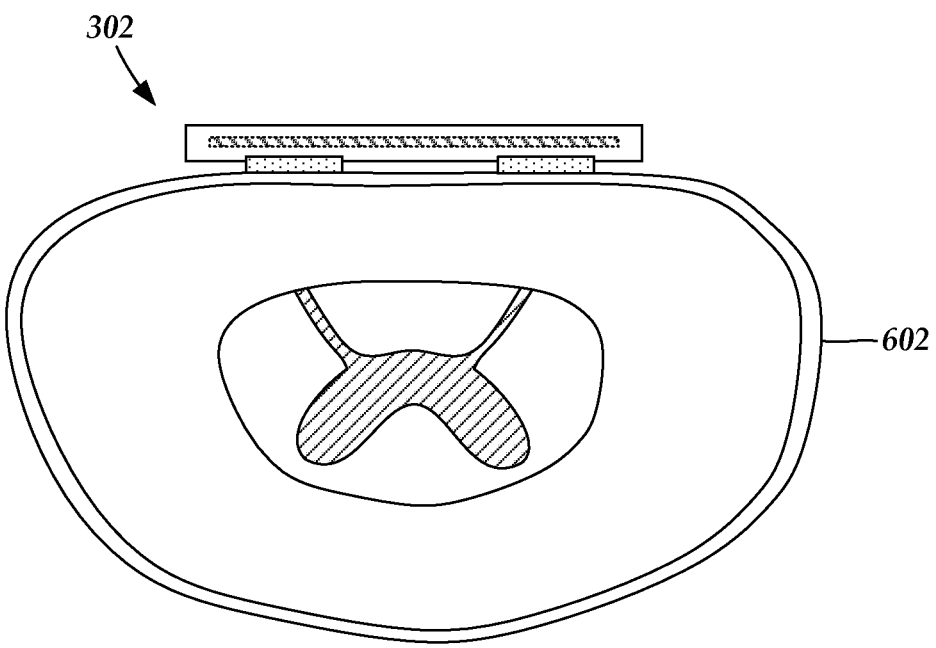
FIG. 6B is a schematic transverse cross-sectional view of electrodes of the paddle body of FIG. 3A abutting a dura surrounding a spinal cord, the paddle body in a flat configuration and pressed against the dura to align the electrodes with the dura, thereby causing a portion of the dura to flatten, according to the invention.
Figure 6C:
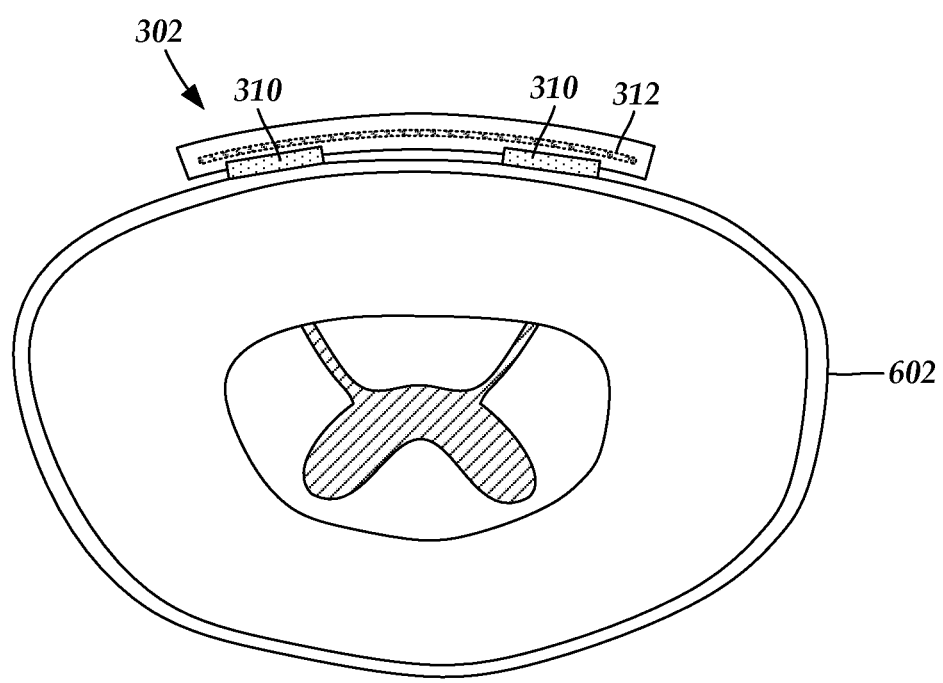
FIG. 6C is a schematic transverse cross-sectional view of electrodes of the paddle body of FIG. 3A abutting a dura surrounding a spinal cord, the paddle body in a bent configuration and pressed against the dura to align electrodes on the paddle body with the dura without flattening the dura, according to the invention.

In at least some embodiments, a paddle body may be implanted against one or more curved anatomical structures within a patient, such as against a portion of the patient's dura in order to provide stimulation to the patient at one or more desired levels of the patient's spinal cord. FIGS. 6A-6C are schematic transverse cross-sectional views of the paddle body 302 positioned in an epidural space such that the front face 304 of the paddle body abuts a dura 602 surrounding a spinal cord 604. In FIG. 6A the paddle body 302 is in a flat configuration. When the paddle body 302 is in a flat configuration and positioned against a curved anatomical structure, the electrodes disposed on the paddle body may not align with the contours of the curved anatomical structure. For example, as shown in FIG. 6A, the electrodes 310 do not align with the contours of the dura 602.

In some cases, the paddle body may be pressed against the curved anatomical structure to improve the alignment of the electrodes of the paddle body with the curved anatomical structure. For example, FIG. 6A shows arrows 606 illustrating a direction that the paddle body 302 may be pressed to improve the alignment of the electrodes 310 with the dura 602. FIG. 6B is a schematic transverse cross-sectional view of the paddle body 302 pressing against the dura 602 such that the paddle body 302 causes a portion of the dura 602 to flatten to conform to the shape of the paddle body 302. Flattening a naturally curved anatomical structure may cause one or more ill-effects, such as physical damage to the anatomical structure, or decreased or improper functioning of the anatomical structure or one or more other structures.

In preferred embodiments, the one or more shape-retaining members are bent to a shape conforming to the shape of the anatomical structure to which the paddle body is to be implanted against prior to implantation. FIG. 6C is a schematic transverse cross-sectional view of the one or more shape-retaining members 312 in bent configurations, thereby causing the paddle body 302 to form a bent configuration. The one or more shape-retaining members 312 are bent into shapes that correspond to the natural curve of the dura 602 at the location where the paddle body 302 is implanted. The one or more bent shape-retaining members 312 cause corresponding bends to be maintained by the paddle body 302. Consequently, the electrodes 310 of the paddle body 302 align with the dura 602 without unnecessarily flattening the dura 602.

Figure 7A:
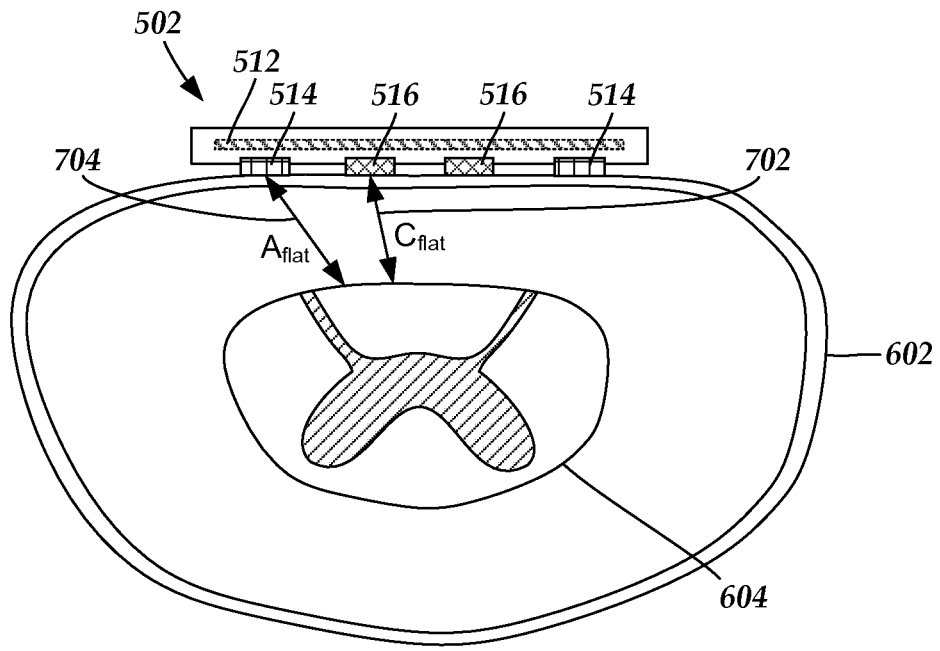
FIG. 7A is a schematic transverse cross-sectional view of electrodes of the paddle body of FIG. 5A abutting a dura surrounding a spinal cord, the paddle body in a flat configuration and pressed against the dura to align the electrodes with the dura, thereby causing a portion of the dura to flatten, according to the invention.
Figure 7B:
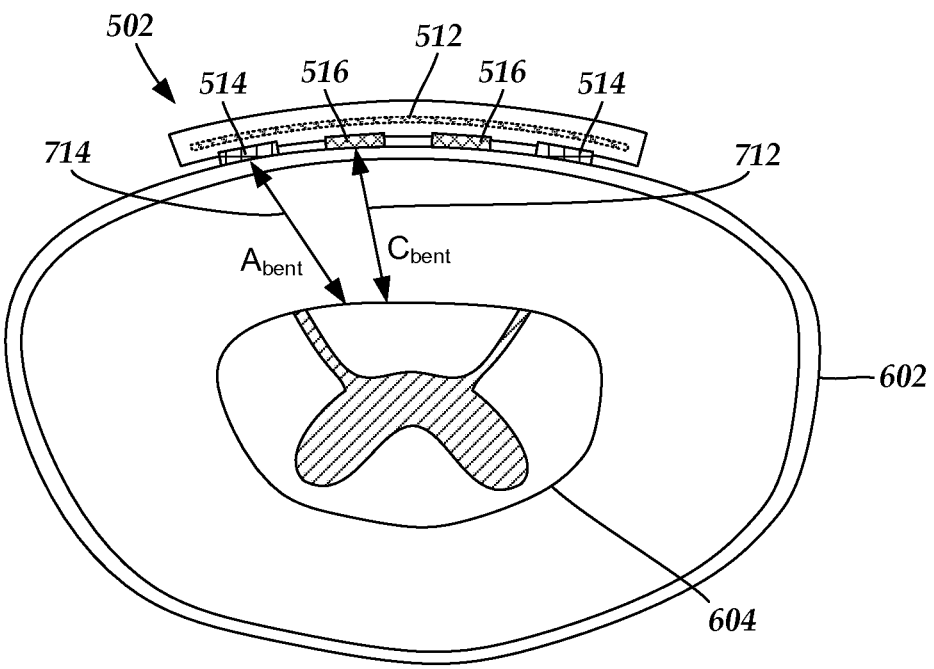
FIG. 7B is a schematic transverse cross-sectional view of electrodes of the paddle body of FIG. 5A abutting a dura surrounding a spinal cord, the paddle body in a bent configuration and pressed against the dura to align electrodes on the paddle body with the dura without flattening the dura, according to the invention.

It will be understood that the bending of the shape-retaining members may similarly be performed with paddle bodies having any type of electrode arrangement. FIGS. 7A and 7B are schematic transverse cross-sectional views of the paddle body 502 abutting the dura 602 surrounding a spinal cord 604. In FIG. 7A the paddle body 502 is shown in a flat configuration and pressing against the dura 602 such that the dura 602 is at least partially flattened. In FIG. 7B, the paddle body 502 is shown in a bent configuration and abutting the dura 602 such that the existing curve of the dura 602 is maintained.

Using a bent paddle lead to provide electrical stimulation to a patient may also improve the efficacy of the electrical stimulation. For example, during transverse tripolar stimulation, when the paddle body 502 is in a flat configuration, as shown in FIG. 7A, the distance between the cathode 516 and the spinal cord 604 (shown in FIG. 7A by two-headed arrow 702) may be substantially greater than the distance between a flanking anode 514 and the spinal cord (shown in FIG. 7A by two-headed arrow 704). Accordingly, the relatively close distance of the cathode 516 to the spinal cord 604, as compared to the anode 514, may reduce the amplitude of electrical stimulation. Consequently, during transverse tripolar stimulation the comparatively close distance from cathode 516 to the spinal cord 604 may attenuate the relative strength of electrical stimulation by the flanking anode 514.

In contrast, when, as shown in FIG. 7B, the paddle body 502 is bent to conform to the existing curve of the dura 602, the distance between the cathode 516 and the spinal cord 604 (shown in FIG. 7B by two-headed arrow 712) may be substantially similar to the distance between a flanking anode 514 and the spinal cord (shown in FIG. 7B by two-headed arrow 714), thereby increasing the relative strength (or the efficacy) of the flanking anode 514.

Figure 8:
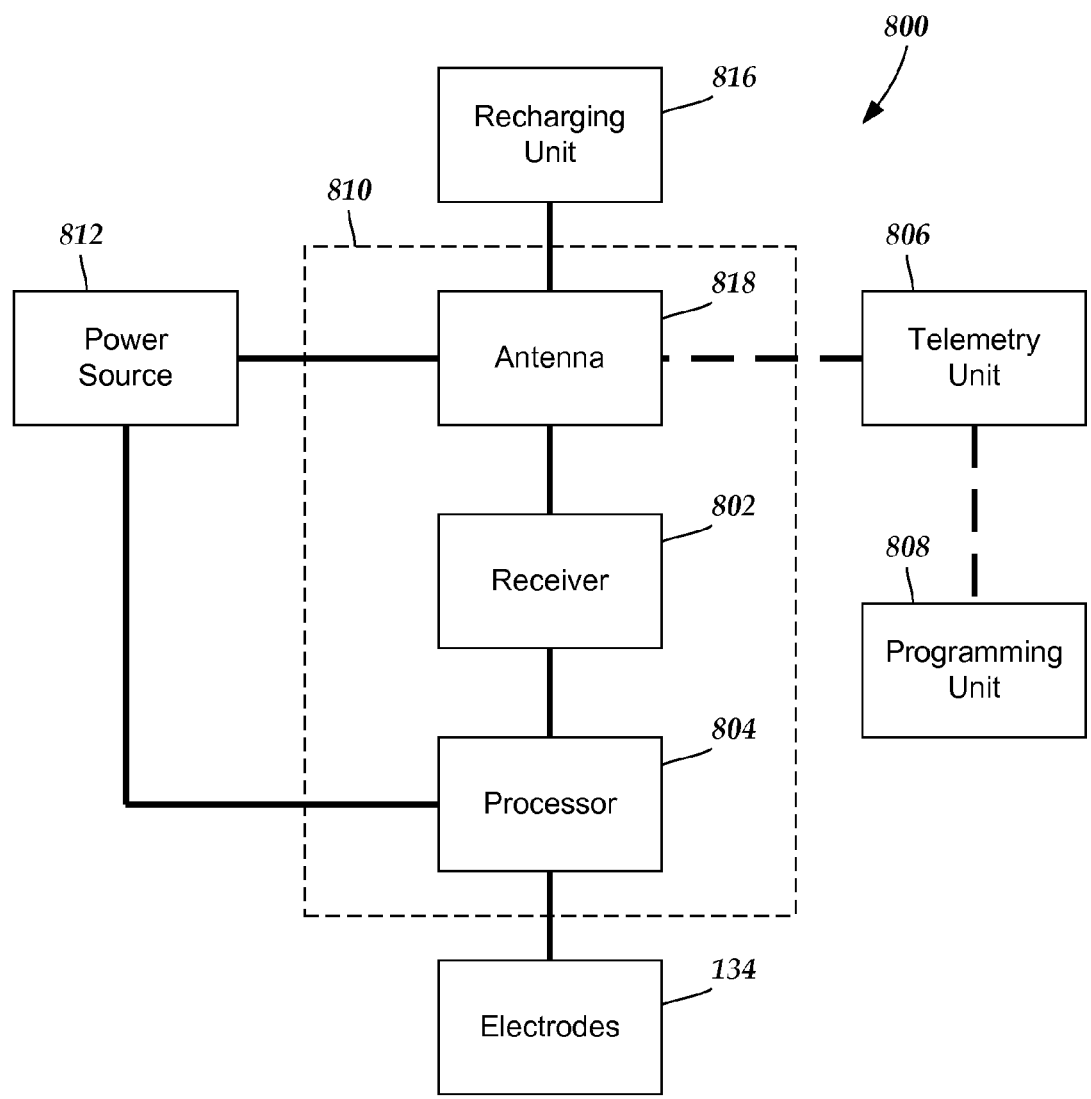
FIG. 8 is a schematic overview of one embodiment of components of a stimulation system, including an electronic subassembly disposed within a control module, according to the invention.

FIG. 8 is a schematic overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in the stimulator references cited herein.

Some of the components (for example, power source 812, antenna 818, receiver 802, and processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 804 is generally included to control the timing and electrical characteristics of the electrical stimulation system. For example, the processor 804 can, if desired, control one or more of the timing, frequency, strength, duration, and waveform of the pulses. In addition, the processor 804 can select which electrodes can be used to provide stimulation, if desired. In some embodiments, the processor 804 may select which electrode(s) are cathodes and which electrode(s) are anodes. In some embodiments, the processor 804 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802 which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806 which is programmed by a programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and receiver 802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system does not include an antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable paddle lead comprising:
    an elongated lead body with a proximal end and a distal end;
    a plurality of terminals disposed at the proximal end of the lead body;
    a paddle body coupled to the distal end of the lead body, the paddle body having a length, a width, and front surface, the paddle body disposed in a flat configuration;
    a plurality of contacts disposed on the front surface of the paddle body;
    at least one manually-bent, adjustable shape-retaining member interconnected with the paddle body, the at least one shape-retaining member formed from a deformable material, wherein the at least one shape-retaining member is interconnected with the paddle body such that bending the at least one shape-retaining member into a bent configuration causes the paddle body to bend from the flat configuration into a corresponding bent configuration, wherein the paddle lead is configured and arranged for implantation into a patient with the paddle body disposed in the bent configuration, wherein the plurality of contacts are configured and arranged to stimulate patient tissue while the paddle body is disposed in the bent configuration, wherein the at least one shape-retaining member is stiff enough to maintain the same bent configuration of the at least one paddle body for at least one day after implantation of the paddle lead, and wherein the bent configuration that the at least one shape-retaining member is configured and arranged for bending the paddle body into prior to implantation of the paddle lead into the patient corresponds to a shape of a portion of an anatomical structure disposed at, or in proximity to, a target stimulation region within the patient; and a plurality of conductors, each conductor electrically coupling at least one of the contacts to at least one of the terminals.

2. The paddle lead of claim 1, wherein the at least one shape-retaining member is interconnected with the paddle body such that the at least one shape-retaining member is disposed at least partially within the paddle body.

3. The paddle lead of claim 1, wherein the at least one shape-retaining member is disposed entirely within the paddle body.

4. The paddle lead of claim 1, wherein the at least one shape-retaining member is disposed entirely external to the paddle body and is coupled thereto.

5. The paddle lead of claim 1, wherein the at least one shape-retaining member extends across at least 75% of the width of the paddle body.

6. The paddle lead of claim 1, wherein the at least one shape-retaining member extends across at least 75% of the of length of the paddle body.

7. The paddle lead of claim 1, wherein the at least one shape-retaining member extends around a portion of the paddle body.

8. The paddle lead of claim 1, wherein the plurality of contacts disposed on the front surface of the paddle body comprises at least one anode and at least one cathode.

9. The paddle lead of claim 1, wherein the deformable material is stiff enough to maintain a given shape for at least one year.

10. The paddle lead of claim 1, wherein the deformable material is separate from and distinct from the paddle lead.

11. An electrical stimulation system comprising
the paddle lead of claim 1;
a control module configured and arranged to electrically couple to the proximal end of the lead body, the control module comprising
a housing, and
an electronic subassembly disposed in the housing; and
a connector for receiving the lead body, the connector having a proximal end, a distal end, and a longitudinal length, the connector configured and arranged to receive the lead body, the connector comprising
a connector housing defining a port at the distal end of the connector, the port configured and arranged for receiving the proximal end of the lead body, and
a plurality of connector contacts disposed in the connector housing, the connector contacts configured and arranged to couple to at least one of the plurality of terminals disposed on the proximal end of the lead body.

12. The electrical stimulation system of claim 11, further comprising a lead extension having a proximal end and a distal end, the connector disposed on the distal end of the lead extension.

13. The electrical stimulation system of claim 12, wherein the proximal end of the lead extension is configured and arranged for insertion into another connector.

14. A method for implanting a paddle lead into a patient, the method comprising:

providing an implantable paddle lead comprising
an elongated lead body with a proximal end and a distal end;
a plurality of terminals disposed at the proximal end of the lead body;
a paddle body coupled to the distal end of the lead body, the paddle body having a length, a width, and front surface, the paddle body disposed in a flat configuration;
a plurality of contacts disposed on the front surface of the paddle body;
at least one manually-bent, adjustable shape-retaining member interconnected with the paddle body, the at least one shape-retaining member formed from a deformable material, wherein the at least one shape-retaining member is interconnected with the paddle body such that bending the at least one shape-retaining member into a bent configuration causes the paddle body to bend from the flat configuration into a corresponding bent configuration, wherein the paddle lead is configured and arranged for implantation into a patient with the paddle body disposed in the bent configuration, wherein the plurality of contacts are configured and arranged to stimulate patient tissue while the paddle body is disposed in the bent configuration, and wherein the at least one shape-retaining member is stiff enough to maintain the same bent configuration of the at least one paddle body for at least one day after implantation of the paddle lead; and
a plurality of conductors, each conductor electrically coupling at least one of the contacts to at least one of the terminals;
bending the at least one shape-retaining member of the paddle lead, wherein bending the at least one shape-retaining member causes the paddle body of the paddle lead to bend from the flat configuration into a bent configuration that conforms to at least a portion of an internal anatomical structure of the patient;
inserting the paddle lead, with the paddle body disposed in the bent configuration, into the patient such that at least a portion of the paddle body abuts the anatomical structure; and
electrically stimulating the anatomical structure using at least one of the plurality of contacts while the paddle body is disposed in the bent configuration;
wherein the at least one shape-retaining member is stiff enough to maintain the paddle body in the same bent configuration for at least one day.

15. The method of claim 14, wherein bending the at least one shape-retaining member comprises bending the paddle body into a bent configuration that conforms to at least a portion of the patient's dura mater.

16. The method of claim 14, wherein inserting the paddle lead into the patient such that at least a portion of the paddle body abuts the anatomical structure comprises inserting the paddle lead into the patient such that at least one of the plurality of contacts abuts the anatomical structure.

17. The method of claim 16, wherein bending the at least one shape-retaining member comprises bending the paddle body into a bent configuration such that at least one of the plurality of contacts is directed towards a target stimulation region in, on, or in proximity to the anatomical structure.

18. The method of claim 17, wherein insetting the paddle lead into the patient such that at least one of the contacts abuts the anatomical structure comprises inserting the paddle lead into the patient such that at least one cathode and at least one anode abut the anatomical structure.

19. The method of claim 18, wherein inserting the paddle lead into the patient such that at least one cathode and at least one anode abut the anatomical structure comprises inserting the paddle lead into the patient such that at least one of the at least one cathodes and at least one of the at least one anodes are disposed along a given width of the paddle body and are positioned a similar distance from the target stimulation region.

* * * * *